(12) United States Patent
Tepper

(10) Patent No.: US 6,663,385 B2
(45) Date of Patent: Dec. 16, 2003

(54) ORTHODONTIC SNAP-IN BRACKET

(76) Inventor: Harry W. Tepper, 19116 Village 19, Camarillo, CA (US) 93012

( * ) Notice: Subject to any disclaimer, the term of this patent is extended or adjusted under 35 U.S.C. 154(b) by 92 days.

(21) Appl. No.: 10/023,299

(22) Filed: Dec. 20, 2001

(65) Prior Publication Data

US 2003/0118967 A1 Jun. 26, 2003

(51) Int. Cl.[7] ................................................ A61C 3/00
(52) U.S. Cl. ........................................... 433/11; 433/8
(58) Field of Search ........................... 433/11, 8, 9, 10, 433/12, 13, 14, 15, 16, 17

(56) References Cited

U.S. PATENT DOCUMENTS

| | | | | |
|---|---|---|---|---|
| 3,043,007 | A | * 7/1962 | Wallshein | 433/8 |
| 3,052,027 | A | * 9/1962 | Wallshein | 433/9 |
| 3,084,437 | A | * 4/1963 | Neger | 433/11 |
| 3,464,112 | A | * 9/1969 | Silverman et al. | 433/11 |
| 3,855,701 | A | * 12/1974 | Le Clair | 433/11 |
| 5,221,202 | A | * 6/1993 | James | 433/9 |
| 5,356,289 | A | 10/1994 | Watanabe | 433/8 |
| D373,638 | S | 9/1996 | Colbert | D24/180 |
| 5,597,302 | A | * 1/1997 | Pospisil et al. | 433/8 |
| 5,607,299 | A | 3/1997 | Nicholson | 433/8 |
| 5,653,588 | A | * 8/1997 | Moschik | 433/8 |
| 5,813,853 | A | * 9/1998 | Kesling | 433/8 |
| 5,993,205 | A | 11/1999 | Heiser et al. | 433/8 |
| 6,217,321 | B1 | 4/2001 | Kanno | 433/11 |
| 6,276,931 | B1 | 8/2001 | DeLeo | 433/9 |

* cited by examiner

*Primary Examiner*—John J. Wilson
(74) *Attorney, Agent, or Firm*—Gordon K. Anderson

(57) ABSTRACT

An orthodontic bracket (20) is taught configured in such a manner that an archwire (48) may be snapped into place retaining the bracket labially on a patients tooth. The bracket has a base plate (22) with a pair of inwardly facing upstanding integral angular legs (46) formed within the base plate transverse to its mesial-distal axis. The legs project the full width of the base plate flush with its sides and are spaced apart essentially the narrowest width of a conventional archwire. The top angular legs have a gap (50) therebetween to allow the archwire to enter. Together with the base plate and the inside surface of the legs, a cavity (52) is formed, dimensioned to receive and retain the archwire. The cavity bottom (56) is parallel with the labial-buccal surface (24) of the base plate and either the legs or the cavity include one or more indentations to assure a proper snap-in effect. The bracket is extruded of a material having sufficient resiliency to arcuately spread apart allowing an archwire to be urged therebetween and snap shut into their primary position after an archwire has passed through thereby captivating an archwire therein. The second embodiment adds a spring clip (68) for complementing the snap shut action of the bracket.

19 Claims, 5 Drawing Sheets

ORTHODONTIC SNAP-IN BRACKET

TECHNICAL FIELD

The present invention relates to brackets for orthodontics in general. More specifically to an orthodontic bracket retaining an archwire by snapping it in place eliminating conventional ligation.

BACKGROUND ART

Previously, many types and shapes of orthodontic brackets have been used in endeavoring to provide an effective means to urge teeth into the desired position when held captive with a archwire.

A search of the prior art did not disclose any patents that possess the novelty of the instant invention, however the following U.S. patents are considered related:

| U.S. Pat. No. | Inventor | Issue Date |
|---|---|---|
| 6,276,931 | DeLeo | Aug. 21, 2001 |
| 6,217,321 | Kanno | Apr. 17, 2001 |
| 5,993,205 | Heiser et al. | Nov. 30, 1999 |
| 5,607,299 | Nicholson | Mar. 4, 1997 |
| 5,356,289 | Watanabe | Oct. 18, 1994 |
| Des.373,638 | Colbert | Sep. 10, 1996 |

DeLeo in U.S. Pat. No. 6,276,931 teaches a basically conventional orthodontic bracket with spaced apart upstanding walls which provide a slot for engaging a retainer band to hold an archwire in place. One of the slots has a ridge or narrow portion on its bottom surface to facilitate the bending of the archwire and the increased height which applies a rotational force on the tooth upon which it is resting.

U.S. Pat. No. 6,217,321 issued to Kanno is for a orthodontic bracket that includes a pressing spring to hold the archwire in place. The pressing spring includes a pressing portion which has a length bridging the slots and is bent at both ends the same direction as to bridge the slots. A pair of upright portions are formed at the tip ends to rise upright along the outer sides of the slots.

Heiser et al. in U.S. Pat. No. 5,993,205 disclose an orthodontic bracket having a base plate with an edge formed to extend parallel with the mesial and distal secants of a tooth crown to facilitate conformity with the anatomy of the tooth's crown.

Nicholson in U.S. Pat. No. 5,607,299 teaches an orthodontic bracket with tie wings having a central recess therebetween. A separate jig may be positioned between the tie wings for positioning the bracket properly on an individuals tooth.

Watanabe in U.S. Pat. No. 5,356,289 discloses an orthodontic bracket having no tie wings at all and is made of a shape memory alloy or resin. In lieu of the tie wings nail portions, spaced well inside the main body, hold an archwire with high efficiency permitting the size of the bracket to be reduced. The basic shape of the bracket has not changed from the conventional form.

For background purposes and as indicative of the art to which the invention is related reference may be made to the design U.S. Pat. No. Des.373,638 issued to Colbert.

DISCLOSURE OF THE INVENTION

Brackets have been in use in the orthodontic discipline since its inception to correct misalignment of patients teeth. Many and varied types of brackets have been developed and are presently in common usage. Almost all of the available conventional prior art brackets are bulky and project a considerable distance labially toward the inside of the wearers lips causing unnecessary discomfort to the wearer. Further the bracket must be tied with a ligature which causes binding of the archwire to the bracket creating forces on the tooth that unintentionally could have the potential to align the tooth in an unwanted direction.

It is therefore a primary object of the invention to have a bracket that is considerably flatter and is configured with a smoother profile. This object is achieved by the use of an extruded bracket that has a pair of inwardly facing upstanding angular legs integrally formed within a base plate projecting the full width of the base plate, flush with its right and left side. Therefore instead of the four separate legs that are commonly used today, the invention employs only a pair of legs that traverse the entire length of the bracket eliminating any irregular surface having the propensity to trap food particles. Further the cavity for the archwire formed by the legs is parallel with the base plate which eliminates completely the raised portion that spaces the archwire away from the tooth common to most brackets available in today's market. The combination of the straightforwardness and simplicity of the smooth uninterrupted legs and the flat bracket make the invention incomparably more comfortable to the user in the labial and buccal regions.

An important object of the invention that there is less friction between the wire and the bracket allowing the archwire to glide laterally within the cavity providing the proper stress to be applied to the tooth by the bracket without any indirect interference.

Another object of the invention is that the archwire is much easier to install and saves time since the wire is simply placed on top of the legs and manually snapped into place into the cavity and is held restrained along the entire width of the bracket. Two people are not necessary to position and hold archwire to connect the ligature as is presently necessary, which requires the so called, four handed dentistry. It may plainly be seen that the invention saves considerable time and expense for the orthodontic practitioner.

Still another object of the invention allows rotating movements of the patients teeth to be accomplished readily in any degree as angulated brackets producing no friction are disclosed by the inventor and are easily adapted to the manufacturing extrusion techniques used.

Yet another object of the invention is the economy of production since the bracket is manufactured by extruding thermoplastic or metal and then cutting the extrusion into individual pieces using methods well known in the art. The cost savings relative to the conventional process now in common usage is extensive and along with the labor economy mentioned previously, the overall combined expense is considerably reduced.

These and other objects and advantages of the present invention will become apparent from the subsequent detailed description of the preferred embodiment and the appended claims taken in conjunction with the accompanying drawings.

BEST MODE FOR CARRYING OUT THE INVENTION

Figure 1:
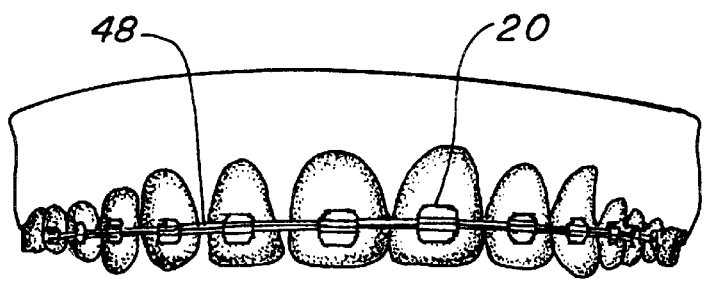
FIG. 1 is a partial isometric view of a typical patients teeth with the invention in the preferred embodiment attached thereto with an archwire.
Figure 2:
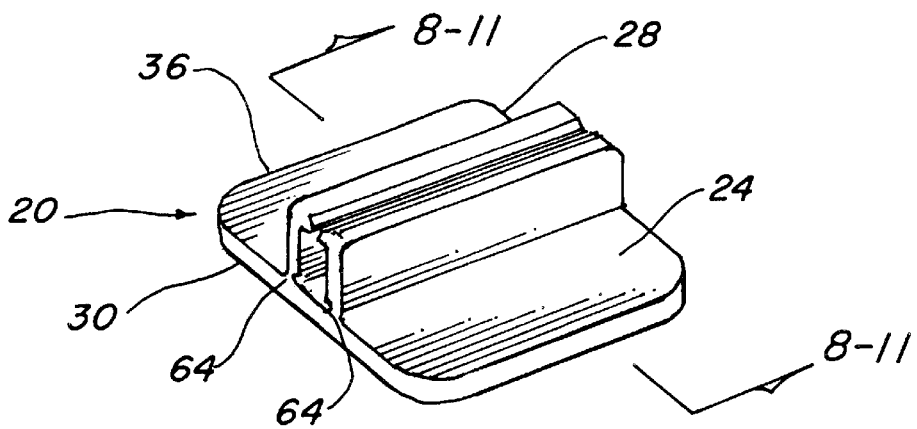
FIG. 2 is a partial isometric view of the preferred embodiment.
Figure 3:
FIG. 3 is a top view of the preferred embodiment.
Figures 4, 5, 6:
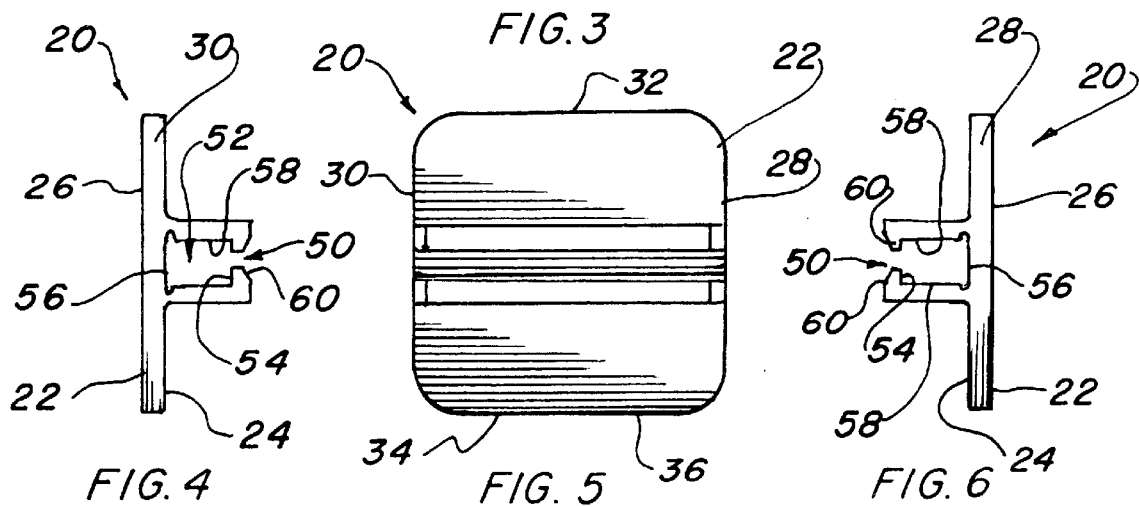
FIG. 4 is a right side elevation view of the preferred embodiment.
FIG. 5 is a plan view of the preferred embodiment.
FIG. 6 is left side elevation view of the preferred embodiment.
Figure 7:
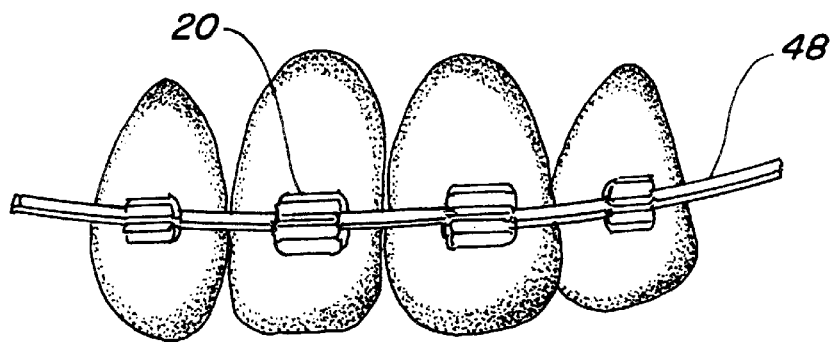
FIG. 7 is a partial isometric view of four patients teeth with the invention in the preferred embodiment attached thereto with an archwire.
Figure 8:
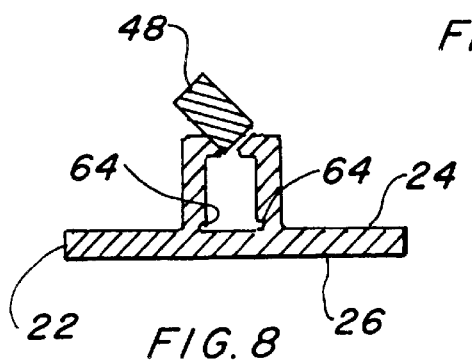
FIG. 8 is a cross sectional view taken along the centerline illustrating an archwire placed in a position ready for installation.
Figure 9:
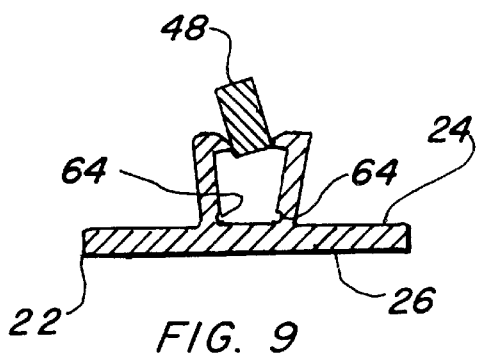
FIG. 9 is a cross sectional view taken along the centerline illustrating an archwire being forced into the gap between the legs during installation.
Figure 10:
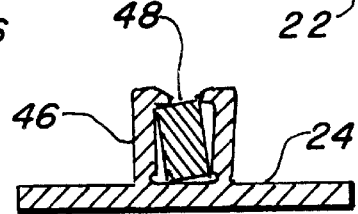
FIG. 10 is a cross sectional view taken along the centerline illustrating an archwire almost in position during installation.

The best mode for carrying out the invention is presented in terms of a preferred and a second embodiment. The preferred embodiment of the orthodontic bracket, shown in FIGS. 1 thorough 28, is configured to allow an archwire to be snapped into place and retain the archwire labially in the bracket on a patients tooth.

Figure 12:
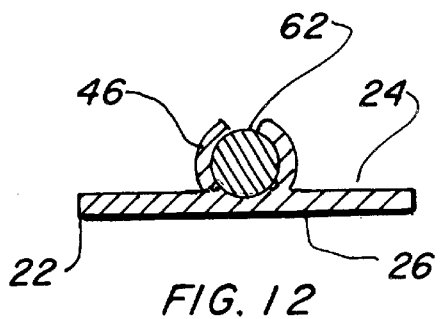
FIG. 12 is a cross sectional view taken along the centerline illustrating a round archwire installed.
Figure 13:
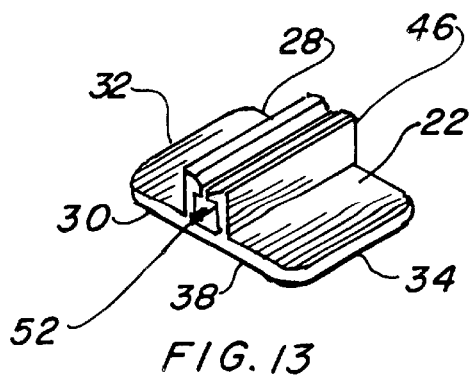
FIG. 13 is a partial isometric view of an embodiment in the rectangular shape base plate.
Figure 14:
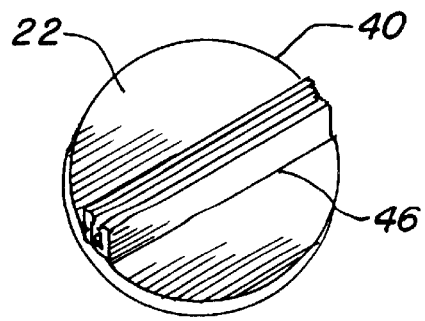
FIG. 14 is a partial isometric view of an embodiment in the round shape base plate.

The bracket 20 is comprised of a base plate 22 having a labial-buccal surface 24, a tooth abutment surface 26, a right side 28, a left side 30, a upper side 32 and a bottom side 34. The shape of the base plate 22 may be square 36, as shown in FIGS. 2–6 and 12, rectangular 38, as depicted in FIG. 13, round 40 as illustrated in FIG. 14 or any other shape having a size appropriate for mounting onto a human tooth. While other methods of manufacture are workable the preferable type of construction uses the extrusion process which is the most economically feasible. This extrusion process is accomplished by melting the material and forcing the melt through a die then instantly cooled thereby forming a continuous strip of material in the chosen configuration. The strip of extruded material may then be cut or sawed into the desired length and the severed ends deburred using well known processes.

Figure 15:
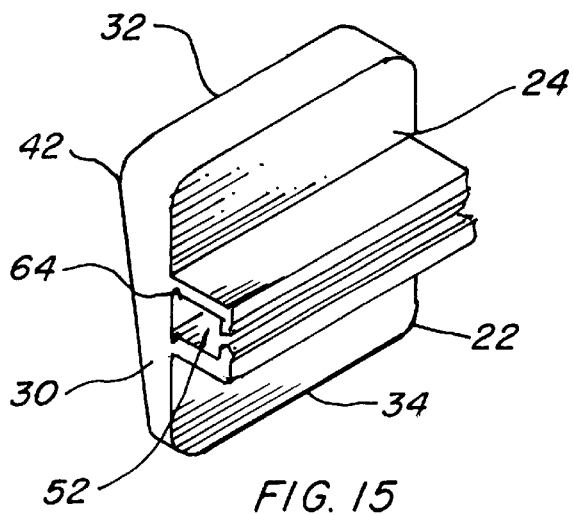
FIG. 15 is a partial isometric view of an embodiment with vertical angulation on the base plate.
Figure 16:
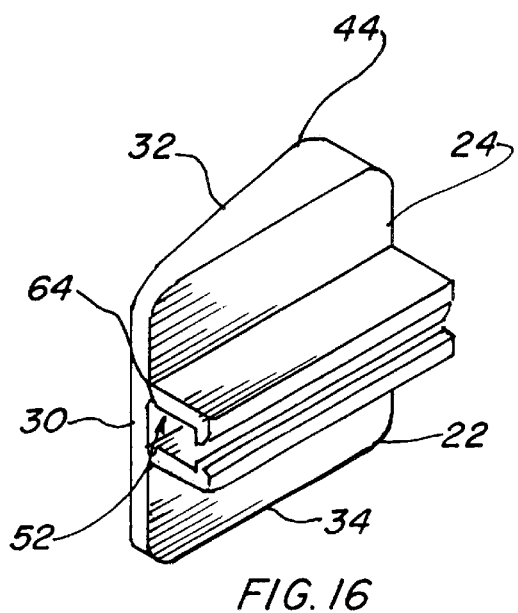
FIG. 16 is a partial isometric view of an embodiment with horizontal angulation on the base plate.

The thickness of the base plate 22 may vary according to the application however the drawings depict the approximate relationship with the remainder of the bracket. In order to include the necessary utility for the bracket 20 it must be configured to rotate the tooth in the desired direction therefore the bracket must have the base plate 22 angled. This angulation may be accomplished by two methods, first the base plate 22 may have one side thicker than the other as shown in FIGS. 15 and 16 with FIG. 15 illustrating the angulation in the direction of a patients tooth occlusal plane 42 which may be incorporated into the shape of the die. FIG. 16 illustrates an angulation in a direction of a patients tooth mesial-distal axis 44 which may be formed using a thick base plate 22 and cutting away the material after the extrusion is formed.

The second method shown in FIGS. 17 and 18 which changes the portions attached to the base plate 22 will be discussed later since the elements have not been described as yet.

Figure 11:
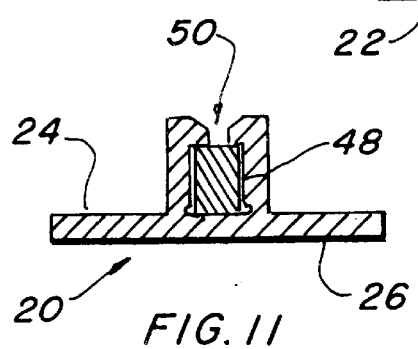
FIG. 11 is a cross sectional view taken along the centerline illustrating an archwire positioned fully into the cavity with the legs snapped back into place.

A pair of inwardly facing upstanding angular legs 46 are integrally formed within the base plate 22 essentially transverse to its mesial-distal axis. The legs 46 project from the base plate the full width therefore are flush with its right and left side. The legs 46 are spaced apart at least the narrowest width of a conventional so called edgewise archwire 48 as shown in FIG. 11. The angular legs 46 have a gap 50 therebetween, preferably from 50 to 60 percent of the archwire's width, allowing the archwire 48 to enter.

The legs 46 and base plate 22 cooperatively form a cavity 52 dimensioned to receive and retain the archwire 48 as illustrated in FIG. 11. This cavity 52 includes a top 54, a bottom 56 and an inside surface 58 with the cavity bottom parallel with the labial-buccal surface 24 of the base plate 22. The cavity 52 is sized to permit the archwire to fit tightly within and yet still permit the legs 46 to accomplish a snap action when the archwire 48 is fully engaged into the cavity.

The angular legs 46 preferably include a bevel 60 on the distal end to assist in spreading the legs when a archwire is urged through the existing gap 50 as shown in FIGS. 8–11. While the invention is directed to the use of a edgewise arch wire a round archwire 62 may also be utilized as shown in FIG. 12 applying all of the same principles.

In order to assure the appropriate snap action of the legs 46 each angular leg may have at least one indentation 64 either within the cavity's inside surface 58 or the outside surface of the leg 46 permitting each leg to properly bend at an angle when urged apart by the archwire 48. FIGS. 19–28 illustrate various locations and combinations of the indentations 64 that are possible to achieve the optimum utility.

Figure 19:
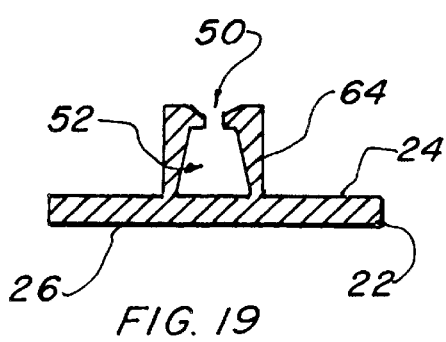
FIG. 19 is a cross sectional view taken along the centerline illustrating a large tapered indentation running the fill length of the cavity inside surface.
Figure 20:
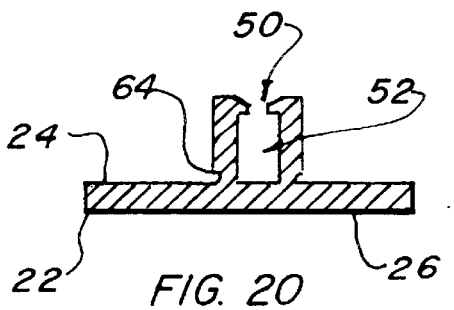
FIG. 20 is a cross sectional view taken along the centerline illustrating an indentation at the outside of the legs.
Figure 21:
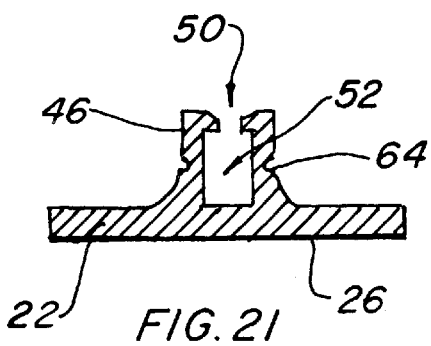
FIG. 21 is a cross sectional view taken along the centerline illustrating a pair of indentations at the median of the outside surface of the legs.
Figure 22:
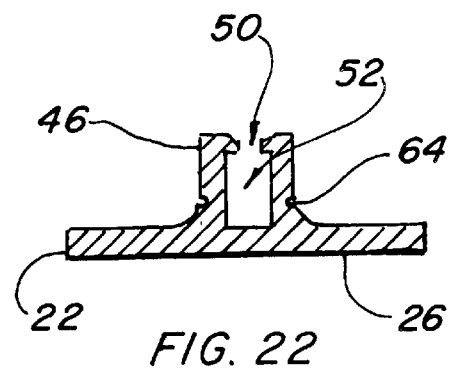
FIG. 22 is a cross sectional view taken along the centerline illustrating a pair of indentations at the lower quadrant on the outside surface of the legs.
Figure 23:
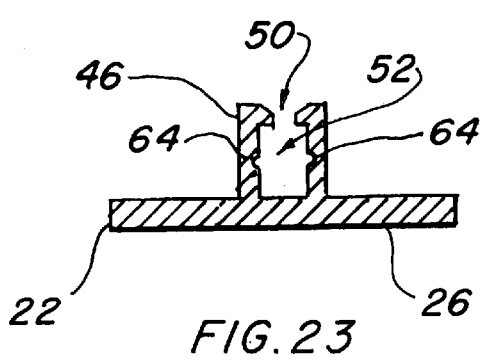
FIG. 23 is a cross sectional view taken along the centerline illustrating a pair of indentations at the median of the inside surface of the cavity.
Figure 24:
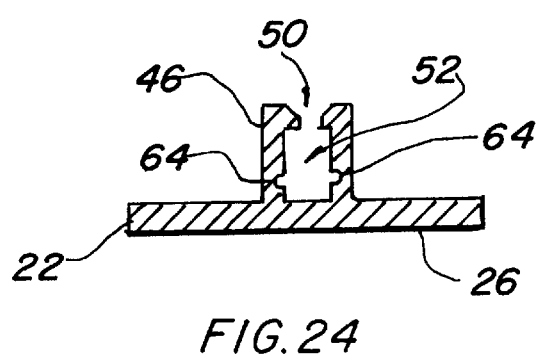
FIG. 24 is a cross sectional view taken along the centerline illustrating a pair of indentations at the lower quadrant of the inside surface of the cavity.
Figure 25:
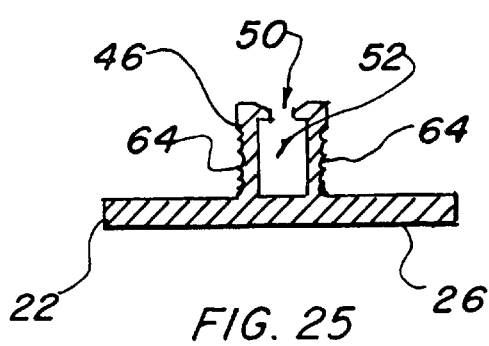
FIG. 25 is a cross sectional view taken along the centerline illustrating an a plurality of indentations within the outside surface of both legs.
Figure 26:
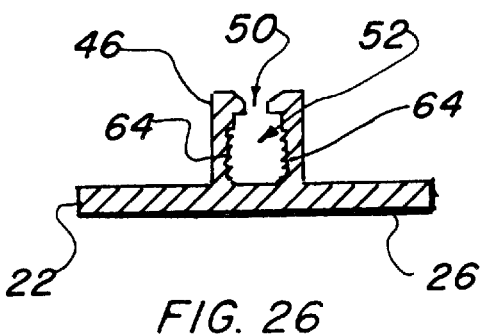
FIG. 26 is a cross sectional view taken along the centerline illustrating an a plurality of indentations on the inside surface of the cavity.
Figure 27:
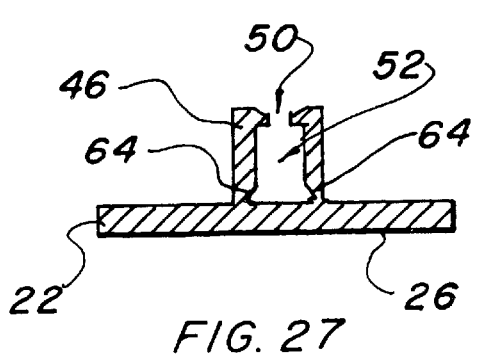
FIG. 27 is a cross sectional view taken along the centerline illustrating a pair of v-shaped groove indentations on the inside of the cavity.
Figure 28:
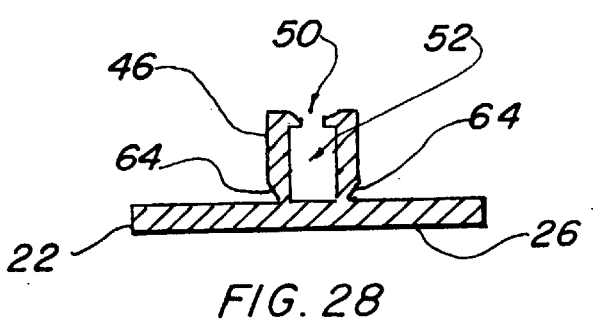
FIG. 28 is a cross sectional view taken along the centerline illustrating a pair of v-shaped groove indentations on the outside of the legs.
Figure 29:
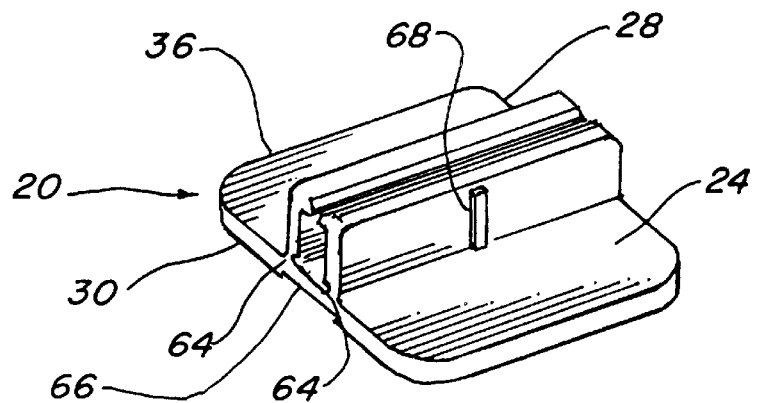
FIG. 29 is a partial isometric view of the second embodiment.
Figures 30, 31, 32:
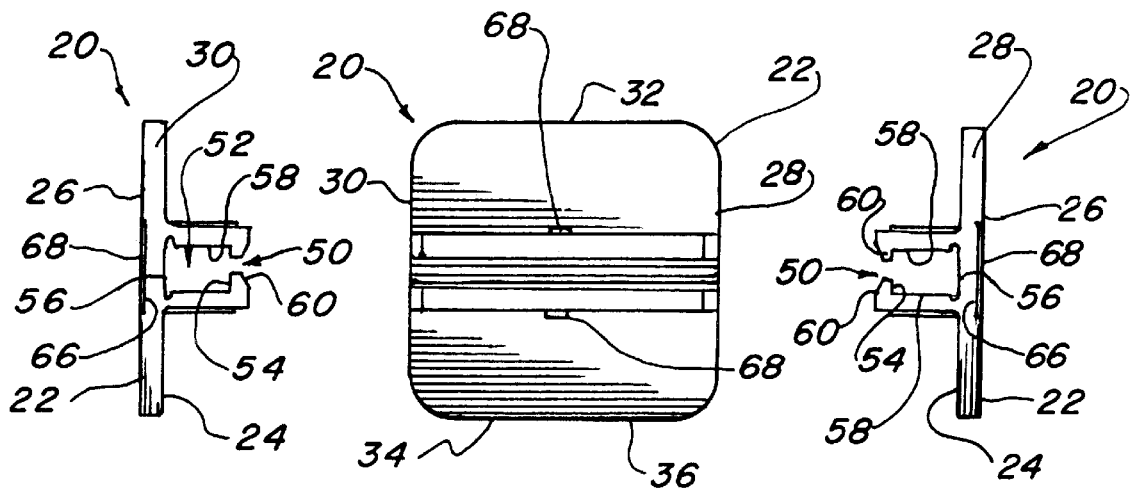
FIG. 30 is a left side elevation view of the second embodiment.
FIG. 31 is a plan view of the second embodiment.
FIG. 32 is right side elevation view of the second embodiment.
Figure 33:
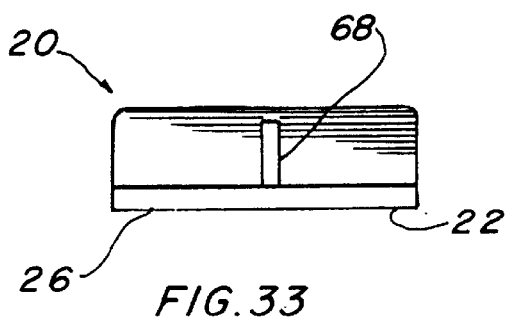
FIG. 33 is a bottom view of the second embodiment.
Figure 34:
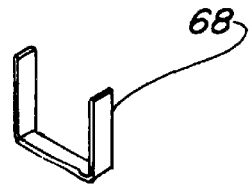
FIG. 34 is a partial isometric view of the spring clip completely removed from the invention for clarity.

FIG. 19 shows a large tapered indentation 64 running the full length of the cavity inside surface 58. FIG. 20 shows a single indentation 64 on the leg outside surface where it intersects with the base plate 22. FIG. 21 illustrates a pair of indentations 64 at the median of the outside surface of the legs 46. FIG. 22 shows a pair of indentations 64 at the lower quadrant on the outside surface of the legs 46. FIG. 23 depicts a pair of indentations 64 at the median of the inside surface 58 of the cavity 52. FIG. 24 illustrates a pair of indentations 64 at the lower quadrant of the inside surface 58 of the cavity 52. FIG. 25 is a cross sectional view taken along an imaginary centerline illustrating an a plurality of indentations 64 within the outside surface of both legs 46. FIG. 26 shows a plurality of indentations 64 on the inside surface of the cavity 52. FIG. 27 depicts a pair of v-shaped groove indentations 64 on the inside of the cavity 52. FIG. 28 illustrates a pair of v-shaped groove indentations 64 on the outside of the legs 46. It is clearly seen that the combinations are almost limitless however the invention anticipates the use of indentations or at least a thinning of the material to assure that the legs 46 function to their optimum efficiency.

Figure 17:
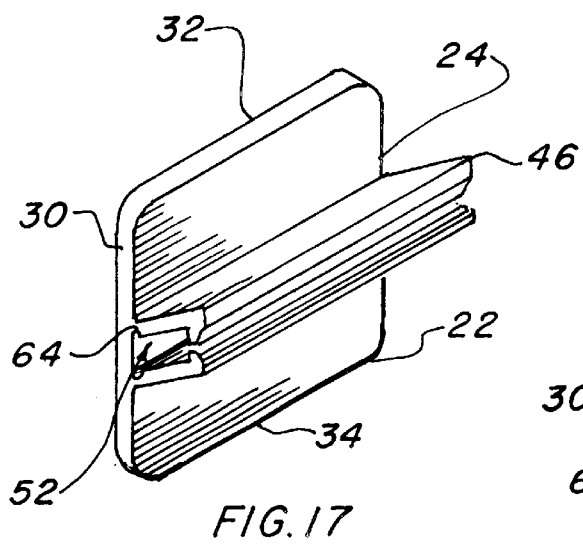
FIG. 17 is a partial isometric view of an embodiment with angular alignment of the legs.
Figure 18:
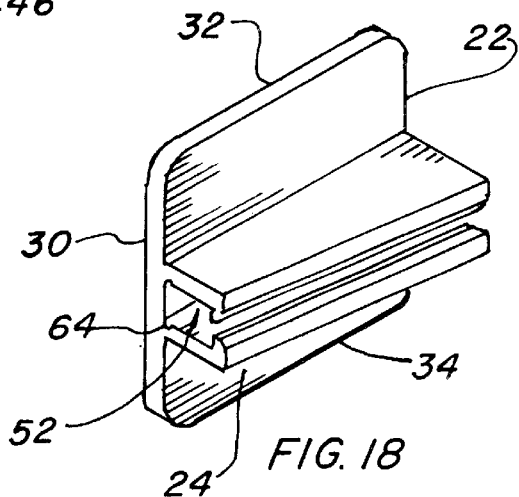
FIG. 18 is a partial isometric view of an embodiment with the legs horizontally angulated.

Now that the elements have been described in detail, the second method shown in FIGS. 17 and 18 which changes the portions attached to the base plate 22 may now be explained. The legs 46 may be angled as shown in FIG. 17 which places torsional forces upon the tooth being rotated. This alteration is easily accomplished in the extrusion die and various angles may be separately made by simply using a different die. FIG. 18 illustrates the legs 46 horizontally angulated which may be achieved by modifying the bracket after it has been extruded which includes milling, or cutting away, the cavity 52 at an angle and tapering the top surface of the legs 46. Other configurations to accomplish angulation may also be used with equal ease.

The orthodontic bracket 20 may be constructed of a thermoplastic material or a metallic material using the extrusion process. Again various materials may be used according to the application and for specific requirements.

For thermoplastic construction the material may have a visual characteristic or being transparent, optically clear, translucent or having a human tooth color. The type of thermoplastic material may be polycarbonate, acrylic, polyester, polymide, polyphenylene, polyethylene, polystyrene, polypropylene, polyvinylchloride, nylon or any other suitable substance having similar characteristics.

The orthodontic bracket 20 constructed of a metallic material may be spring steel, stainless steel, a pseudoelastic material such as heat activated nickel titanium or cold activated copper titanium all of which are well known in the art and in common usage.

In application the brackets 20 are bonded to the labial side of the tooth and the archwire 48 is forced into the cavity 52 between the legs 46 through the gap 50. The legs 46 separate and allow the archwire 48 to enter and when fully engaged the legs 46 snap together securing the bracket in place while still leaving sufficient clearance for lateral movement of the archwire.

The second embodiment is illustrated in FIGS. 29–34 and is basically the same as the preferred embodiment except a stiffening or reinforcing member has been added to supplement the snap acting feature of the legs 46. The base plate 22, in this embodiment, contains a centrally located recess 66 on the tooth abutment surface parallel with the legs 46 and at least one u-shaped spring clip 68 is disposed through the base plate 22 from the tooth abutment surface parallel and contiguously engaging an outside surface of the upstanding angular legs 46 as shown in the drawings. The spring clip 68 is shown by itself in FIG. 34 and consists of a metallic substance such as spring steel or the like. The recess 66 is formed in the extruding process and the clip 68 is inserted into the edges of the recess under heat and pressure allowing the clip to penetrate the material of the base plate 22 in the thermoplastic option. A pair of slots may be pierced in the material in the metallic option. In any event the recess 66 is the same depth as the thickness of the clip 68 permitting the bottom portion of the bracket 20 to be flush with the labial-buccal surface of a patients tooth. While only one clip 68 is illustrated, a plurality may also be employed, positioned adjacent to the legs 46 spaced apart along the recess 66.

While the invention has been described in complete detail and pictorially shown in the accompanying drawings, it is not to be limited to such details, since many changes and modifications may be made to the invention without departing from the spirit and scope thereof. Hence, it is described to cover any and all modifications and forms which may come within the language and scope of the appended claims.

What is claimed is:

1. An orthodontic bracket configured such that an archwire may be snapped into place retaining the archwire in the bracket labially on a patients tooth comprising, a base plate having a labial-buccal surface, a tooth abutment surface, a right side, a left side, an upper side and a lower side, a pair of inwardly facing upstanding angular legs integrally formed within the base plate essentially transverse to the base plates mesial-distal axis, projecting a full width from the base plate therefore flush with the base plates right side and left side, also spaced apart at least an archwires narrowest width, said angular legs having a gap therebetween with said angular legs and base plate forming a cavity dimensioned to receive and retain an archwire, said cavity having a top, a bottom and an inside surface with the cavity bottom parallel with the labial-buccal surface of the base plate, and said orthodontic bracket base and integral angular legs formed of a material having sufficient resiliency to arcuately spread apart allowing an archwire to be urged therebetween and snap shut into their primary position after an archwire has passed through thereby captivating an archwire therein.

2. The orthodontic bracket as recited in claim 1 further wherein said orthodontic bracket further constructed by an extrusion process.

3. The orthodontic bracket as recited in claim 1 wherein said base plate is square in shape of a size appropriate for mounting onto a human tooth.

4. The orthodontic bracket as recited in claim 1 wherein said base plate is rectangular in shape of a size appropriate for mounting onto a human tooth.

5. The orthodontic bracket as recited in claim 1 wherein said base plate is round in shape of a size appropriate for mounting onto a human tooth.

6. The orthodontic bracket as recited in claim 1 wherein said base plate has an angulation in a direction of a patients tooth occlusal plane.

7. The orthodontic bracket as recited in claim 1 wherein said base plate has an angulation in a direction of a patients tooth mesial-distal axis.

8. The orthodontic bracket as recited in claim 1 wherein said angular legs having a bevel on a distal end to assist in spreading the legs when a archwire is urged therebetween.

9. The orthodontic bracket as recited in claim 1 wherein said cavity formed by said angular legs is sized to permit an archwire to fit tightly within and yet allowing the legs to accomplish a snap action when the archwire is fully engaged into the cavity.

10. The orthodontic bracket as recited in claim 1 wherein said gap between the angular legs is from 50 to 60 percent of an archwire width.

11. The orthodontic bracket as recited in claim 1 wherein said cavity is dimensioned to receive and retain an edgewise archwire.

12. The orthodontic bracket as recited in claim 1 wherein said cavity is dimensioned to receive and retain a round archwire.

13. The orthodontic bracket as recited in claim 1 wherein said bracket is constructed of a thermoplastic material having a visual characteristic selected from the group consisting of transparent material, optically clear material and translucent material.

14. The orthodontic bracket as recited in claim 1 wherein said bracket is constructed of a thermoplastic material having a human tooth color.

15. The orthodontic bracket as recited in claim 1 wherein said bracket is constructed of a thermoplastic material selected from the group consisting of polycarbonate, acrylic, polyester, polymide, polyphenylene, polyethylene, polystyrene, polypropylene, polyvinylchloride and nylon.

16. The orthodontic bracket as recited in claim 1 wherein said bracket is constructed of a metallic material selected from the group consisting of spring steel, stainless steel, heat activated nickel titanium, and cold activated copper titanium.

17. An orthodontic bracket configured such that an archwire may be snapped into place retaining the archwire in the bracket labially on a patients tooth comprising, a base plate having a labial-buccal surface, a tooth abutment surface, a right side, a left side, an upper side and a lower side, a pair of inwardly facing upstanding angular legs integrally formed within the base plate essentially transverse to the base plates mesial-distal axis, projecting a full width from the base plate therefore flush with the base plates right side and left side, also spaced apart at least an archwires narrowest width, wherein each angular leg having at least one indentation on said cavity inside surface permitting each leg to bend angularly when urged apart by a archwire, said angular legs having a gap therebetween with said angular legs and base plate forming a cavity dimensioned to receive and retain an archwire, said cavity having a top, a bottom and an inside surface with the cavity bottom parallel with the labial-buccal surface of the base plate, and said orthodontic bracket base and integral angular legs formed of a material having sufficient resiliency to arcuately spread apart allowing an archwire to be urged therebetween and snap shut into their primary position after an archwire has passed through thereby captivating an archwire therein.

18. An orthodontic bracket configured such that an archwire may be snapped into place retaining the archwire in the bracket labially on a patients tooth comprising, a base plate having a labial-buccal surface, a tooth abutment surface, a right side, a left side, an upper side and a lower side, a pair of inwardly facing upstanding angular legs integrally formed within the base plate essentially transverse to the base plates mesial-distal axis, projecting a full width from the base plate therefore flush with the base plates right side and left side, also spaced apart at least an archwires narrowest width, wherein each angular leg having at least one indentation on an outside surface of each leg permitting said leg to bend angularly when urged apart by a archwire, said angular legs having a gap therebetween with said angular legs and base plate forming a cavity dimensioned to receive and retain an archwire, said cavity having a top, a bottom and an inside surface with the cavity bottom parallel with the labial-buccal surface of the base plate, and said orthodontic bracket base and integral angular legs formed of a material having sufficient resiliency to arcuately spread apart allowing an archwire to be urged therebetween and snap shut into their primary position after an archwire has passed through thereby captivating an archwire therein.

19. An orthodontic bracket configured such that an archwire may be snapped into place retaining the archwire in the bracket labially on a patients tooth comprising, a base plate having a labial-buccal surface, a tooth abutment surface, a right side, a left side, a upper side and a lower side, a pair of inwardly facing upstanding angular legs integrally formed within the base plate essentially transverse to the base plates mesial-distal axis, projecting a full width from the base plate therefore flush with said base plates right side and left side, also spaced apart at least an archwires narrowest width, said angular legs having a gap therebetween with said angular legs and base plate forming a cavity dimensioned to receive and retain an archwire, said cavity having a top, a bottom and an inside surface with the cavity bottom parallel with the labial-buccal surface of the base plate, said orthodontic bracket base and integral angular legs formed of a material having sufficient resiliency to arcuately spread apart allowing an archwire to be urged therebetween and snap shut into their primary position after an archwire has passed through thereby captivating an archwire therein, and at least one u-shaped spring clip disposed through the base plate from the tooth abutment surface parallel with the upstanding angular legs for complementing the legs snap shut action.

* * * * *